(12) United States Patent
Takahashi

(10) Patent No.: US 8,661,599 B2
(45) Date of Patent: Mar. 4, 2014

(54) SPHERICAL BRUSH

(76) Inventor: Atsushi Takahashi, Fukui (JP)

(*) Notice: Subject to any disclaimer, the term of this patent is extended or adjusted under 35 U.S.C. 154(b) by 239 days.

(21) Appl. No.: 12/747,976

(22) PCT Filed: Dec. 12, 2008

(86) PCT No.: PCT/JP2008/072608
§ 371 (c)(1),
(2), (4) Date: Jun. 14, 2010

(87) PCT Pub. No.: WO2009/078349
PCT Pub. Date: Jun. 25, 2009

(65) Prior Publication Data
US 2010/0275399 A1    Nov. 4, 2010

(30) Foreign Application Priority Data

Dec. 14, 2007  (JP) ................................. 2007-323023
Jun. 27, 2008  (JP) ................................. 2008-168245

(51) Int. Cl.
*A46B 9/04*    (2006.01)

(52) U.S. Cl.
USPC ............. 15/167.1; 15/159.1; 15/160; 15/189; 15/206

(58) Field of Classification Search
USPC ............. 15/159.1, 160, 164, 167.1, 189, 206; 300/1, 21
See application file for complete search history.

(56) References Cited

U.S. PATENT DOCUMENTS

| 3,165,362 | A | * | 1/1965 | Glas ................................. 300/21 |
| 4,145,787 | A | * | 3/1979 | Bastian ......................... 15/229.5 |
| 5,329,730 | A | * | 7/1994 | Scheider et al. .............. 451/466 |
| 5,839,146 | A | * | 11/1998 | Chen .............................. 15/114 |
| 6,241,411 | B1 | * | 6/2001 | Brieva et al. .................. 401/129 |

FOREIGN PATENT DOCUMENTS

JP       59-41125    3/1984

* cited by examiner

*Primary Examiner* — Brian Glessner
*Assistant Examiner* — Patrick Maestri

(57) ABSTRACT

[Problem] Disclosed is a method for manufacturing a spherical brush having highly dense brush bristles for easy cleaning of periodontal pockets and a cylindrical brush having the brush bristles highly dense brush bristles at a ball portion of a tip thereof, and a brush manufactured by the manufacturing method.
[Solution means] A fiber bundle, which is composed of a number of short fibers prepared by cutting long fibers, is gripped between a set of U-shaped wires arranged to crisscross with each other to form a loop. The open ends of the U-shaped wires are pulled and twisted in opposite directions, so that the fibers at the portion gripped by the U-shaped wires are compressed to reduce the size of their bundled areas. Elastic repulsion is established between the fiber bundles near a wire-gripped portion by the size differences of the cross sectional areas of the free end fibers at both ends of the wire-gripped portion, and is utilized so that the free end fibers diverge radially to the circumference from the wire-gripped portion.

9 Claims, 9 Drawing Sheets

SPHERICAL BRUSH

BACKGROUND OF THE INVENTION

1. Field of the Invention

The Invention relates to a spherical brush and a manufacturing method thereof, and in particular relates to a manufacturing method for a spherical brush for cleaning, coating of liquids or brushing teeth, and a spherical brush manufactured by the manufacturing method, especially a tooth brush using the spherical brush.

2. Description of the Related Art

In general, in view of cleaning oral cavity and preventing decayed teeth, tartar attached on the teeth is to be removed. To prevent the periodontal disease, one of the two most famous teeth diseases (the other one is decayed teeth), it is important to remove the tartar in the periodontal pocket located between the teeth and gums. To prevent the periodontal disease, the gums are to be massaged and periodontal pocket is to be effectively cleaned, wherein several brushing methods are brought up. The most famous method is to insert the tip of the brush bristles into the periodontal pocket with an angle of 45° with respect to the teeth axis and slightly move the bristles forward and backward, which is named repeated bus method. Corresponding to the brushing technique, tooth brushes of various shapes are developed wherein the tips of brush bristles are processed as far as possible. The tooth brush driven by electronic power is also developed. In addition to shape and material of brush bristles or bristles arrangement direction, the effective cleaning to the periodontal pocket is also discussed.

[Patent Document] JP 59-41125

BRIEF SUMMARY OF INVENTION

However, as described above, the bus method which is an effective brushing technique for the periodontal pocket is to insert the tip of tooth brush into the periodontal pocket and correctly kept at a predetermined angle to vibrate slightly forward and backward, which requires very complicated and high technique. As the tip of the brush bristles is to be inserted into the periodontal pocket easily, a tooth brush having a brush portion in which the planted bristles are arranged in a cylindrical shape. It is necessary to control the brushing direction with respect to the longitudinal axis direction of teeth. Such a brush has no effective technique to insert the tip of brush bristles into the periodontal pocket and cannot clean the periodontal pocket. A teeth gap brush is used as a tool to clean teeth gap portion, periodontal pocket, the brush bristle density of the metal twisted brush is limited by its structure. The shaft formed by the metal twisted portion impacting the teeth cause uncomfortable feeling, and the brush bristle is perpendicular to the shaft.

For this reason, the invention provides a manufacturing method for manufacturing an electronic tooth brush or tooth brush used by hand at large scale, which can be inserted into the surface of teeth in any direction without notifying correct contact angles with respect to the tooth surface of the tooth neck portion so as to insert the tip of brush bristles into periodontal pocket, and moves the brush along the tooth neck portion to clean the tooth surface and periodontal pocket effectively. When the electronic oral cleaning tool is used, to reduce the uncomfortable feeling caused by the resin product vibrating at high speed on the back surface of the experienced bristles planting portion to hit the opposite teeth, the whole head is covered by brush bristles. A brush of high bristle density and cylinder shape without bristles falling off is provided.

This invention relates to a brush with radially diverged brush bristles. The object of the invention can be achieved by the claims of the invention. That is, the invention provides a brush in any brush inserting direction, the brush bristles touch the tooth surface at a correct angle and the tip of the bristles are inserted into periodontal pocket automatically. The tooth brush can be inserted into an oral cavity in any direction and moves forward and backward or rotates therein to clean the surface of teeth and the periodontal pocket. No resin product for supporting the brush bristles is needed, and when used as a clean brush of an electronic oral cleaning tool, the brush is preferably to have radially diverged bristles. The first invention is a spherical brush comprising a set of U-shaped wires of U-loop shape crisscrossing with each other in a central portion, and a fiber bundle comprising a plurality of short fibers, cut from long fibers, disposed in an O-shaped loop formed by the two U-shaped wires being crossover disposed, wherein the fiber bundle is compressed and fixed by pulling the ends of the individual wire in opposite directions. At the same time, the ends of the U-shaped wires are twisted in opposite directions to twist the central O shaped loop and further reduce the size of the cross section area of the fiber bundle disposed in the O loop, and the size differences of cross section area between two free ends fibers of the fiber bundle makes the free end fiber bundle diverging radially from the rough center of the fiber bundle to a circumference, and the shape of the spherical brush is maintained by a maintaining force caused by permanent deformation of the U-shaped wires. The spherical brush is used according to requirement to fold two ends of the twisted wire or cut one end or both ends of the twisted wires near the brush bristle gripped portion inside of the brush bristles. At this time, when the bundle are made of a material of low friction coefficient, the falling off or shifting of the bundle is avoided before a fiber bundle is preliminarily fixed by pulling and compressing. In the second invention, the set of U-shaped wires of a U-loop shape in the first invention are disposed as a knot, and a fiber bundle is preliminarily tied by binding force of the U-shaped wires. By bundling to the knot shape, even the U-shaped wires pulling force is removed in the process, the fiber bundle does not fall off, therefore the U-shaped wires pulling process and the twisting process can be separately performed. Since the U-shaped wires disposed as a knot does not twist during a pulling process, the fiber bundle does not rotate to prevent the falling and shifting of the fiber bundle.

The third invention provides a spherical brush, wherein a folded portion of a U-shaped wire and a stopper form a loop, wherein two ends of the U-shaped wire passing through the stopper respectively to form an O-shape. Similar to the first and second inventions, the substantial center of a longitudinal axis of a fiber bundle composed of short fibers is disposed in the loop. One end of the U-shaped wire is pulled when the stopper is held, whereby the fiber bundle is compressed in the loop formed by the U-shaped wire and the stopper. The elastic repulsion of the fibers near two ends of the compressed fiber is established by the size differences of cross section area between un-compressed fiber bundles near the free end fiber bundle at two sides to make the free end fibers diverging radially from the stopper-wire-gripped portion to circumference. At the same time, the U-shaped wire is twisted with respect to the stopper, and the stopper is fixed by the permanent deformation of the U-shaped wires.

The fourth invention provides a spherical brush, to obtain a cylindrical shaped brush with high brush density and no bristles falling off, and to obtain a string of spherical brushes in the first and second inventions, the free ends of the U-shaped wire form continuous O loops disposed as crossed shape or continuous knots. The fiber bundle is disposed in the crossed portion or knot portion of the U-shaped wires, and the U-shaped wires are twisted to obtain a string of spherical brushes. To obtain the string of the spherical brushes, the third invention is applied to the fourth invention, wherein fiber bundles are reciprocally disposed between two parallel wires which pass through a plurality of stoppers and are compressed by the stoppers. At the same time, the U-shaped wires are rotated preliminarily and deform permanently to fix the stopper.

In the fifth invention, the fibers forming the fiber bundle have partially or uniform different material. Proper mechanical properties are given to any portion of the spherical brush according to requirement. When fibers of different color are used, the spherical brush has a colorful appearance. When the fibers have the same material, fibers of different shape, such as the fibers of different diameters, the short fibers having cross section area varied in the longitudinal direction or the fibers constituting resin fibers clipping in the fiber axial direction, are used, whereby the mechanical properties in the brush or on the surface of the brush are different. The spherical brush can be freely varied by any combination of various fibers constituting the fiber bundle. Even in the string of spherical brushes, each spherical brush may have different type.

Since the radially divergence in all quadrants of the spherical brush is formed by the fibers repulsing each other due to the size differences of fiber density, when the fiber density of the spherical brush is reduced, the divergent angle of the fibers is decreased, whereby the spherical brush cannot be formed. The fifth invention is to solve the problem. The short fibers as in the fourth invention made of the different fiber material having different chemical properties to form the all-quadrant radially diverged spherical brush. Certain specific short fibers, which are easily melted, are selectively melted by a chemical melting process or heating process to make the brush fibers radially diverge in all quadrants.

In addition to the short resin fibers constituting the fiber bundle in the first to the fifth inventions, the seventh invention discloses a spherical brush having brush fibers formed by one or more of the non-woven fabric, porous ribbon, rubber or metal material. Since the non-woven fabric, porous ribbon and rubber have high compressibility, the fibers can easily diverges in all quadrants. By selecting grinding grains according to the material, a grinding function is provided. When metal is used, the permanent deformation of metal is utilized to obtain the all-quadrant divergence.

The eighth invention discloses a spherical brush trimmed to various shapes to provide functions according to the requirement of the spherical brush in the first to seven inventions. The bullet shaped brush is suitable for cleaning a narrow drum space between teeth, and a cylinder shaped brush provides a brushing function accomplished by the periphery surface in addition to the cleaning function provided by the top circular surface.

The ninth invention discloses an element preventing fibers of a semi-spherical brush described in the first to eighth inventions from falling off, wherein the spherical brush is formed by melting and fixing the fiber bundle at one side of wire gripped portion to make the brush bristle diverging toward the opposite side. The semi-spherical brush diverges to an opposite side by welding and fixing one end of the U-shaped wires gripped portion of the fiber bundle. By welding, even no brush fibers on the opposite side of the holding wire, the brush bristles are prevented from being falling off.

The manufacturing method and features of a spherical brush of the invention has the following effects. In the first invention, a spherical brush comprises a set of U-shaped wires of U-shaped loop crisscrossing with each other in a central portion and a fiber bundle comprising a plurality of short fibers cut from long fibers and disposed in an O-looped shape portion formed by the two U-shaped wires crisscrossing with each other, wherein the fiber bundle is compressed by pulling and twisting the ends of the U-shaped wires in opposite directions. At the same time, the ends of the U-shaped wires are twisted in opposite directions to further reduce the size of the cross section area of the fiber bundle, and the cross section area difference between free end fiber bundle makes fibers diverges radially from the center of the fiber bundle to become a radiation shape, and the shape of the spherical brush is maintained by permanent deformation of the U-shaped wires. The twisted wire formed at two ends of the spherical brush is cut by any length at one or both ends of the brush bristle near the gripped portion according to requirement. The spherical brush in which an element having twisted wire staying on one side of the spherical brush is connected to a brush handle, and can keep a correct angle with respect to the tooth surface in any insertion direction of the brush and simply moves forward and backward to clean the tooth surface and periodontal pocket. As there is no resin brush bristles maintaining portion, the one who cannot clean the oral cavity due to disabled body is cleaned by a nurse. At this time, the resin portion does not damage the gums. Even the nurse can perform good oral management. Similarly, the spherical brush is used as an electronic oral cleaning tool and particularly a supersonic electronic brush, because the front portion is covered by spherical bristles, which is like the brush portion of a conventional supersonic electronic tooth brush, no resin portion appears on the brush bristle planting portion, whereby the uncomfortable feeling generated by the resin portion contacting the teeth is prevented.

As long as a spherical brush having brush bristles in all quadrants is obtained by compressing and diverging a fiber bundle mechanically, a semi-spherically diverged brush of high bristle density can be formed, which cannot be carried out by a fiber-planting brush wherein the brush bristles are planted by metal flat thread or round thread passes through holes formed on a conventional resin material. The density of brush bristles are controlled by adjusting the compression property of fibers, the repulsing property of spring fibers and the fiber number of fiber bundle.

The various properties of the spherical brush are formed according to the material and shape of the brush bristles thereof. In particular, when a material of low friction coefficient is used in the fiber bundle, similar to the second invention, U loop shaped wires in the first invention are formed as a knot, and a fiber bundle being inserted into O loop. The fiber bundle is strongly fixed preliminarily by the tie force of the U-shaped wires. When the U-shaped wires of knot shape is pulled, no rotational force occurs, and the shifting or falling of the brush bristle is prevented; thus, raising manufacturing efficiency in each process. Since the fiber bundle is strongly and preliminarily fixed by the knot shape, even the pulling force of the U-shaped wires is released before a twisting process is performed, the fiber bundle is maintained in the gripped condition. The U-shaped wires pulling process and twisting process can be separately performed.

In the first and second inventions, the fiber bundle is disposed in an O loop formed by two U-shaped wires crisscrossing with each other. The ends of the U-shaped wires are pulled and twisted in opposite directions to compress and reduce the size of the cross section area of the fiber bundle, and the free end fibers radially diverges and is fixed by a force generated by the permanent deformation of the U-shaped wires. In the third invention, a loop is formed by a stopper and a folded portion of a U-shaped wire. Two ends of the U-shaped wire pass through the stopper. Similar to the first and second invention, the center of the fiber bundle composed of short fibers is disposed in the loop. Two ends of the U-shaped wire are pulled when the U-shaped wires is held by the stopper, whereby the fiber bundle is compressed in the loop formed by the U-shaped wire and the stopper. The elastic repulsion of the fibers near two ends of the compressed bristles is established by the size differences of cross section area between uncompressed fiber bundles near the free end fiber bundle so that the free end fibers diverge radially from the stopper-wire-gripped portion to circumference. At the same time, the U-shaped wire is twisted with respect to the stopper, and the stopper is fixed by the permanent deformation of the U-shaped wires, and the fiber bundle gripped by the U-shaped wire and the stopper is maintained in compressed condition. Since the twisting of the U-shaped wire for the stopper at this time reduces the loop diameter and provides pulling function, the pulling and twisting processes can be performed simultaneously.

The fourth invention provides a spherical brush, wherein the free ends of the U-looped wire in the first and second invention are connected to form a ring shape. The ring shaped wires crosses each other or is disposed as a knot. The fiber bundle is disposed in the O loop portion formed at two ends of the ring shaped wire, and the U-shaped wires are twisted. Although the distance of spherical brushes is determined by the length of the brush bristle and the total length of the twisted O loop, if the half length of the brush bristle is longer than the total length of the twisted O loop, the U-shaped wires is totally covered by the brush bristle. When the third invention is applied to obtain a string of spherical brushes, the fiber bundle is reciprocally disposed between two parallel wires passing through the stoppers and compressed by the stoppers. At the same time, as the U-shaped wires are preliminarily rotated and deformed permanently to fix the stoppers. Similar to the fourth invention, since the center of the fiber bundle is strongly compressed and held, a cylindrical brush is provided, which has much higher brush bristle density than a typical metal twisted brush but has no brush bristle fall off. The brush bristle type of the continuous spherical brush is that the tip is covered by bristles in all quadrants. When the brush is used as a teeth gap brush, since the U-shaped wires tip is hided as a conventional teeth gap brush, no pain caused by the U-shaped wires contacting the gums occurs and the soft brush bristles covering the tip provide comfortable feeling.

The spherical brush of high density has bristles diverging in all quadrants by performing bulking process on various fibers. In the fifth invention, a part of the short fibers of the fiber bundle for the spherical brush in the first to fourth invention may have different material. According to contact angle and contact strength for the object to be cleaned or grinded, proper functions are provided for the applied method. Furthermore, when the same material is used, a part of the bristles of the spherical brush has different mechanical properties or different divergent shapes by partially disposing a part of short fibers of different diameters, spring fibers crimped in axial direction or short fibers having varied cross section area. For example, the central portion of the fibers of the umbrella shape at both ends are compressed to obtain a spherical brush having a scaled shape on its spherical surface. A spherical brush having different mechanical properties in the brush or on the brush due to the three-dimensional shape of the brush bristles are provided.

The mechanical properties of the spherical brush can be formed freely as the fifth invention. In a string of spherical brushes disposed in the continuous O loops, each fiber bundle may have different function by varying the material, shape and color of each fiber bundle in the continuously disposed spherical brush.

In the sixth invention, the fibers of fiber bundles for the spherical brush may partially or entirely have short fibers having different chemical properties. After the spherical brush is formed by compression and divergence of bristles, the short fibers, which are easily melted, are selectively melted and removed by a chemical melting process or heating process, whereby the brush bristle density is adjusted. In general, when the density of the fiber bundle is reduced, the divergent angle of the brush bristles is decreased. Therefore, a spherical brush diverging in all quadrants is difficult and has the fibers having the amount to form the spherical brush, which radially diverges in all quadrants, comprising two kinds of fibers having different chemical properties. After the brush bristle diverges radially to form the brush, some specific brush bristles are selectively processed by a chemical melting process or heating process, whereby the brush bristle density is decreased and the brush bristles radially diverge in all quadrants. As the melting process is performed from surface to center portion of the spherical brush, the melting depth of the brush bristles is adjustable. In particular, as the highly compressed gripped portion of the U-shaped wires is difficult to reach, the brush bristles can be equally diverged. No severe adjustment in the process is needed.

In the seventh invention, material of the fiber bundle is not limited to various short resin fibers, one or more kinds of the non-woven fabric, porous ribbon, rubber, metal can be the material of the brush bristles, whereby the applications of the spherical brush described in the first to fourth inventions are increased, and proper functions are provided according to the requirement. It is difficult for the material to have a shape of ribbon uniformly developed in whole periphery. The brush having ribbon of non-woven fabric, sponge or rubber holding a spherical center portion is formed by the manufacturing method.

Although the spherical brush has various fiber bristle, as described in the eighth invention, the radially diverged brush bristles are rotatably trimmed or trimmed to various shape with respect to the U-shaped wires axis. They can provides proper functions according to the purpose of the spherical brush described in the first to seventh inventions.

For all of the spherical brushes, the fiber bundle is basically fixed by a holding force generated by a mechanical friction force when the fiber bundle is compressed by the U-shaped wires. As described in the ninth invention, the fiber bundle radially diverging at any side of the U-shaped wires of the spherical brush is melted, whereby the falling off of brush bristle caused by use and material property is prevented. The fiber bundle of the spherical brush is welded or bonded to a resin handle, whereby the spherical brush symmetrical at both sides is inserted into the oral cavity to reach the portion to be cleaned. By the same method, an electronic brush is provided, which is rotatable in the longitudinal and traverse directions and the twisted portion of the spherical brush serves as a maintaining element. The spherical brush is fixed to the tip of driving shaft of the supersonic electronic brush and has 360° arranged brush bristles. The brush bristles of the electronic brush can effectively contact the portion to be cleaned in any inserting direction and at any positioning angle. When the welding portion serves as an axis for the brush bristles to be mounted to the resin handle, a spherical brush with handle is obtained, which is rotatable in the respective direction according to the mount angle with respect to the handle. By regulating the rotational resistance between the brush and the bearing, when the handle is operated to clean an oral cavity, the spherical brush, which gives a rotational resistance by a appropriate pressure, contacts the surface of teeth and gums with a correct pressure and rotates there. The spherical brush rotates properly corresponding to the stress pushing the surface of teeth or gums in a correct cleaning direction to massage and clean the surface of teeth and gums with a proper force, whereby the gums is not to be hurt, a correct cleaning method is established, and the fresh brush surface always contact the portion to be cleaned to raise the cleaning efficiency.

Furthermore, the center of the spherical brush having brush bristles in all directions is mounted to the electronic brush, whereby rotation, repeated rotation, sonic or supersonic vibration is given to perform effective cleaning. In addition to cleaning an oral cavity, the global spherical brush can contact other cleaning surface in any contact direction, especially for a portion having protrusions and depressions. For example, when we see our two dimensional image in a mirror and wash and massage our face, since the skin can be directly contacted by the brush bristle, the brush merely moves and massages the skin to contact the skin with a proper pressure and improve the cleaning ability for small protrusions and depressions, such as hair pore. At this time, as an electronic brush, vibration, sonic or supersonic vibration is given to the spherical brush to improve the effect.

Since the fibers used in the invention is very thin, the operation is a problem. To solve the problem, when a radial brush is formed individually, one end of a small opening of the fiber bundle is preliminarily melted for easy operation. When a string of spherical brushes is formed, the long fibers are enclosed by a shrink film with heat shrink property to hold the fibers which can be operated together. After the fiber bundle held by the shrink film to be integrally formed at any position is tied by the U-shaped wires, the shrink film is removed, and the U-shaped wires are pulled and twisted to obtain a spherical brush.

According to the invention, the spherical brush can be any type depending on the purpose. In addition to the oral cavity product in dental technique, the spherical brush of the invention can also be applied to a distributor for cosmic product, a face wash device or grinding device in industry. When the spherical brush bristles are carried out, the spherical brush has a higher density than the conventional brush.

DETAILED DESCRIPTION OF INVENTION

FIGS. 1-16 show an embodiment of the invention. The same elements in all figures are given the same numbers. Although the basic structure is the same as that of a conventional brush, the features of the spherical brush illustrated in the figures include a substantially longitudinal axis center portion of a fiber bundle being pulled and twisted by a metal wire to compress the fiber bundle, whereby the clearance between fibers of the fiber bundle disappear and the fibers at free end are radially diverged by the size differences between cross section areas of the fibers in the compressed center portion and the fibers at the free ends.

Embodiment 1

Figure 1:
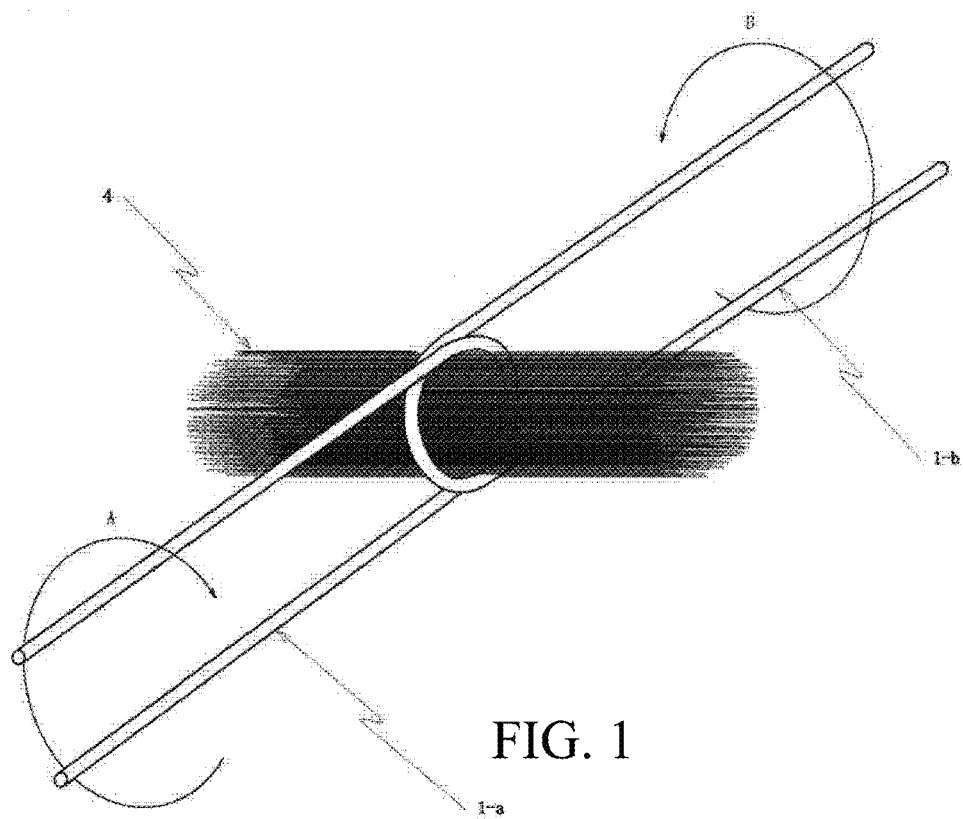
FIG. 1 is a perspective view showing that when a fiber bundle is inserted into a loop formed by U-shaped wires crisscrossing with each other, a part of the fiber bundle is gripped during a manufacturing process of the invention.
Figure 2:
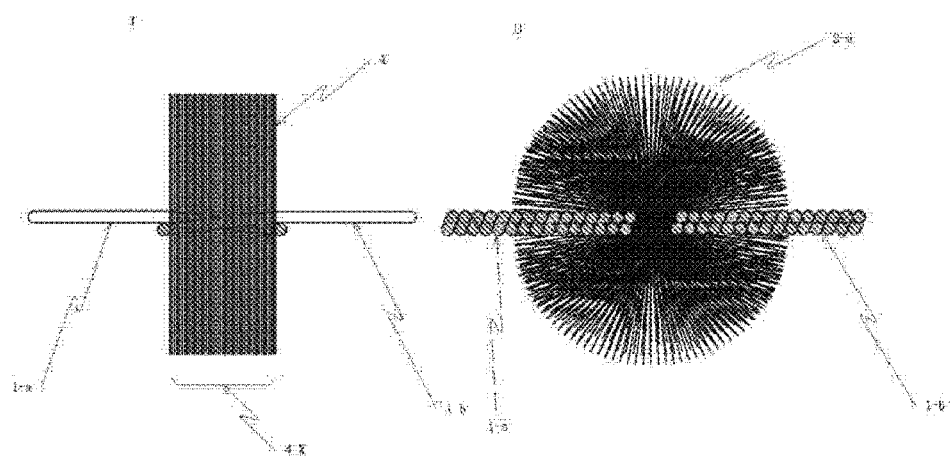
FIG. 2 is a cross section showing the gripped fiber bundle (T) and radial divergence of free end fibers after pulling and twisting of the ends of the U-shaped wire (U) during a manufacturing process of the invention.
Figure 3:
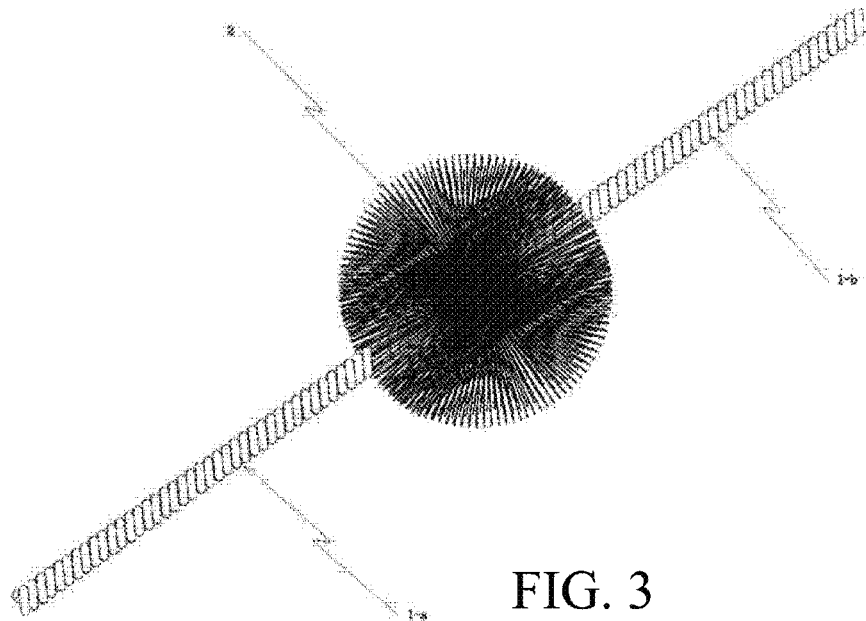
FIG. 3 is a perspective view showing the ends of the U-shaped wires being pulled and twisted to radially diverge the free end fibers.
Figure 4:
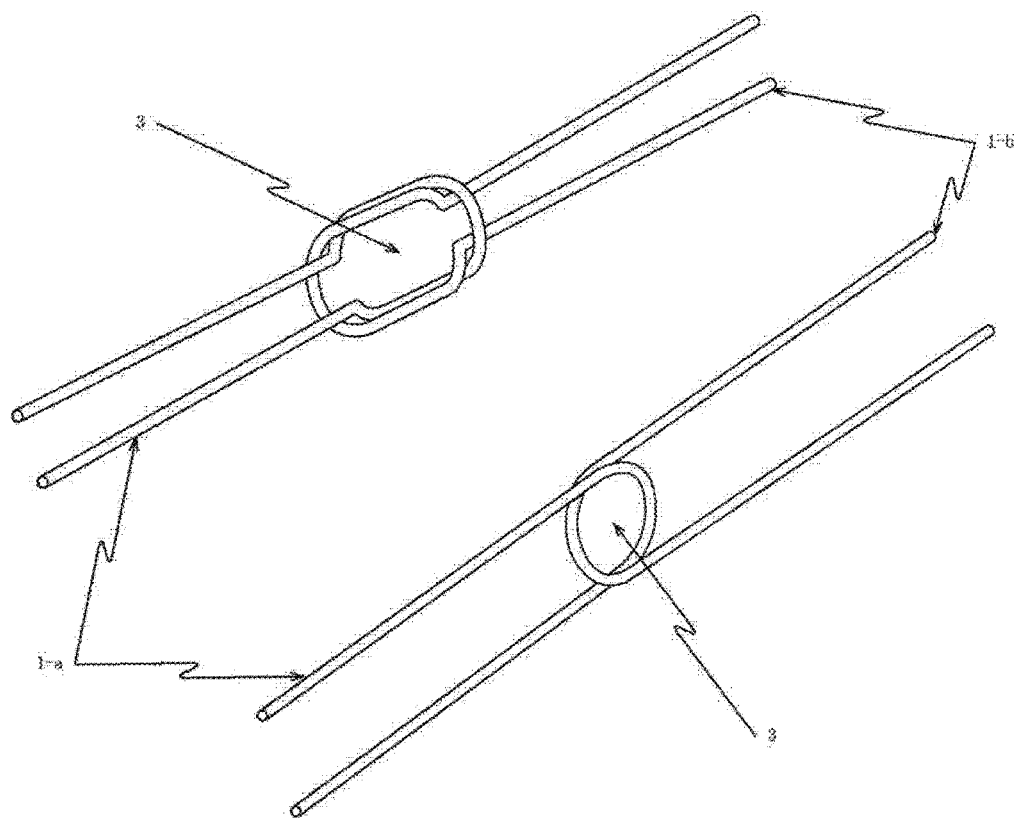
FIG. 4 is a perspective view of the U-shaped wires crisscrossing with each other or arranged as a knot.

In this embodiment, as shown in FIG. 1, polypropylene bulking fibers of 0.02-0.08 mm are cut to a predetermined length according to the requirement of a spherical brush. For example, the fibers are cut to short fibers of about 10 mm for a tooth brush used in an oral cavity. As an example, corresponding to a brush divergence density, a fiber bundle 4-$x$ is formed. As the periphery of the central cross section of a diverging spherical brush is as long as 3.14 times that of the length of the fiber which is considered as the diameter of the central cross section, the divergence cross section length on a single side thereof is half that of the periphery of the central cross section to form the fiber bundle diameter of the compact spherical brush. When 10 mm fibers are used, the diameters of fiber bundle 4-$x$ which are not compressed, preferably exceeds the periphery of 15.7 mm of a single side of the spherical brush. As Shown in FIG. 1, the center of the fiber bundle 1 is disposed in an O loop formed by two U-shaped wires 1-*a*, 1-*b* crisscrossing with each other at a center portion, and the end of the U-shaped wires are pulled in opposite directions. As shown by T in FIG. 2, since the U-shaped wires crisscross with each other, the U-shaped wires tie and compress the fiber bundle 4-*x* so as to grip the fiber bundle, whereby the fibers are prevented from falling off during the manufacturing process. As shown by U in FIG. 2, when two ends of the U-shaped wires are twisted in opposite rotational directions, the cross section area of the fiber bundle 4-*x* is further compressed and reduced, and the free end fibers are radially diverged from the substantially longitudinal axis center portion to the circumference by the size differences of cross section areas to form a spherical brush 2. At the same time, the U-shaped wires are twisted and deformed permanently to fix the brush bristles. As shown in FIG. 3, a spherical brush 2 with wires 1-*a*, 1-*b* twisted at both ends is obtained. According to requirement, the U-shaped wires 1-*a* near the compressed portion is cut to obtain a dandelion-shaped brush with wire 1-*b* on one side. When the U-shaped wires 1-*a*, 1-*b* are all cut, a spherical brush of a cloud shape is obtained. By using the spring-shaped (bulking fiber), the repulsion of the fiber forms the spherical brush having a bristle density high enough to hide the U-shaped wires therein. When fibers of equal amounts are used, the density of the brush bristle is proportional to the compression of fiber bundle and the repulsion of the fibers. Using polypropylene as an example, when fibers of a low friction coefficient, such as Nylon, is used, the U-shaped wires 1-*a*, 1-*b* are disposed as a knot shape to prevent the U-shaped wires from loosening and prevent fibers from falling off. In particular, the process is performed by hand, when the twisting process is performed, so that there is no need to keep pulling the U-shaped wires; thus, raising manufacturing efficiency. For all kinds of fibers, even two ends of the knot arranged wires 1-*a*, 1-*b* is pulled, no twisting occurs; therefore, the fiber bundle is compressed more efficiently and strongly without obstructing the fiber compression process caused by the stiffness of the U-shaped wires and friction force of the metal.

Embodiment 2

Figure 14:
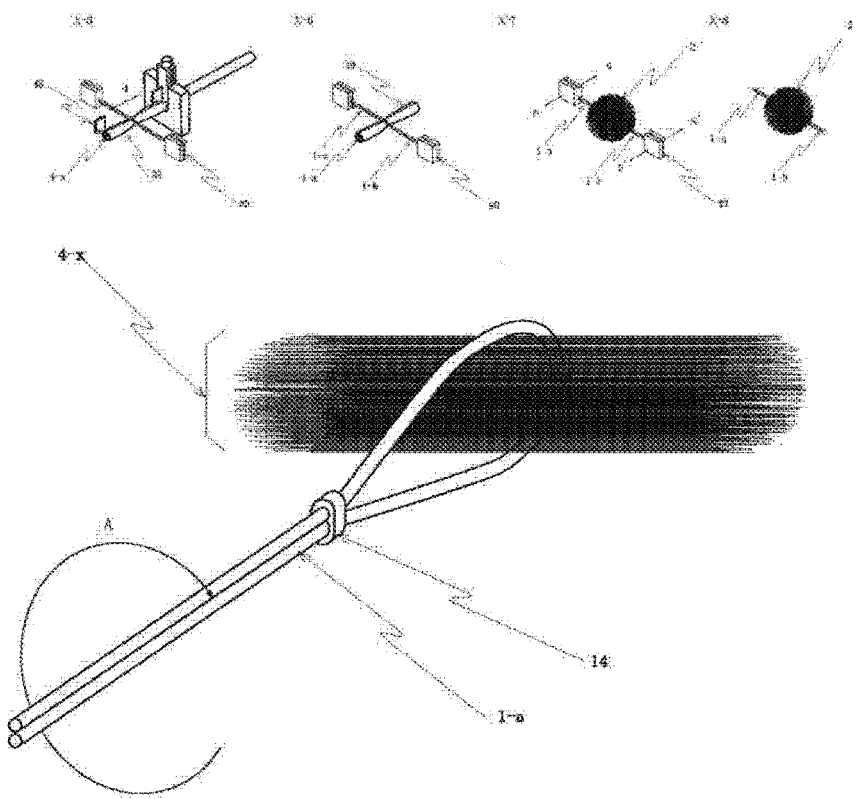
FIG. 14 is a perspective view showing the U-shaped wires being held by a stopper and the center of the fiber bundle being disposed in the loop during a manufacturing process of the invention.
Figure 15:
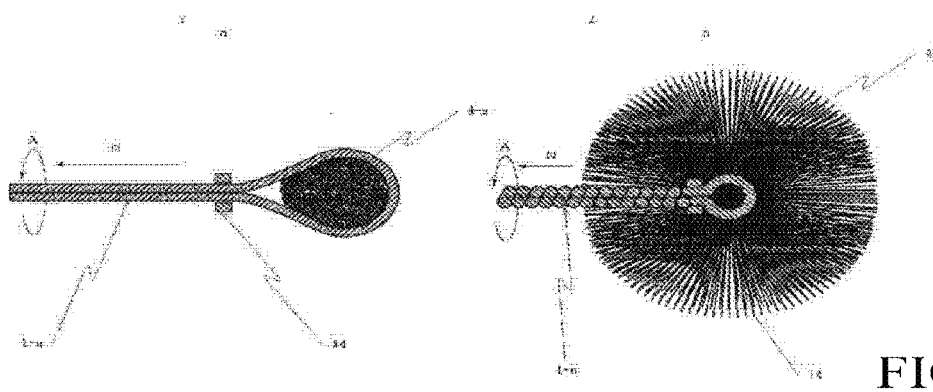
FIG. 15 is a cross section view showing the fiber bundle being gripped (Y) and radial divergence of free end fibers after pulling and twisting of the ends of the U-shaped wire (Z) during a manufacturing process of the invention.
Figure 16:
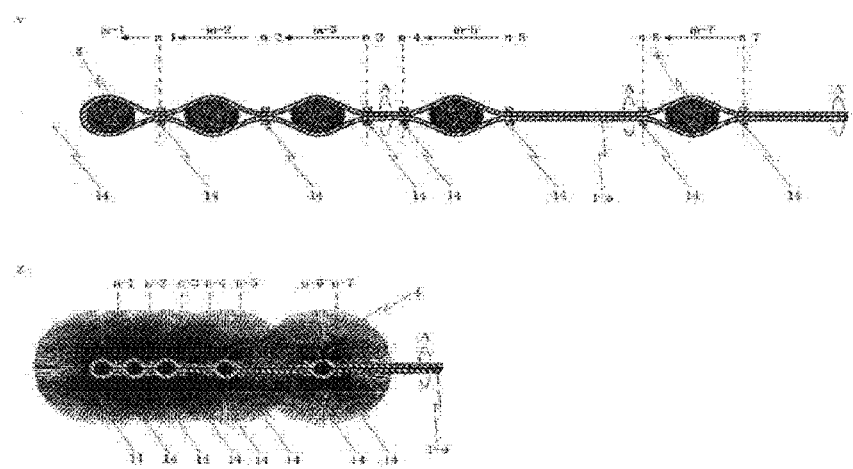
FIG. 16 is a cross section view depicting the set condition (Y) of the stopper, fiber bundle and wires, and the divergence state (Z) of the continuous spherical brushes after compression of the stopper and wire rotation during a manufacturing process of the invention.

In the embodiment of the first and second inventions, a fiber bundle is disposed in the O-shaped loop formed by two U-shaped wires. The ends of the U-shaped wires are pulled and twisted in opposite directions to compress the fiber bundle and reduce the size of the cross section areas. The free end fibers are radially diverged and fixed by a maintaining force generated by the permanent deformation of the wires. In the third embodiment, as shown in FIG. 14, two ends of a U-shaped wire 1-*a* passes through a stopper 14. The substantial center of the fiber bundle 4-*x* comprising short fibers is disposed in the loop formed by the stopper 14 and the U-shaped wire 1-*a*. As shown by Y in FIG. 15, when the stopper 14 is held in position n, two ends of the U-shaped wire are pulled in direction m, and the fiber bundle 4-*x* is compressed. The free end fibers (shown by z in FIG. 15) are radially diverged from the portion gripped by wire and stopper to a circumference by the elastic repulsion of fibers established by the size differences of the cross section area at the fiber bundle areas near the free end fibers at both ends of the portion gripped by wire and stopper which are not compressed. When the U-shaped wire 1-*a* is twisted in a direction A with respect to the stopper 14 fixed in position n, the repulsion of fiber bundle is resisted by the permanent deformation of the U-shaped wires to maintain the periphery of the loop and the diverged spherical brush. Since the pulling process and twisting process of the U-shaped wire 1-*a* is to reduce the diameter of the loop, when the pulling process and twisting process can be performed simultaneously, the spherical brush can be manufactured more efficiently.

Figure 5:
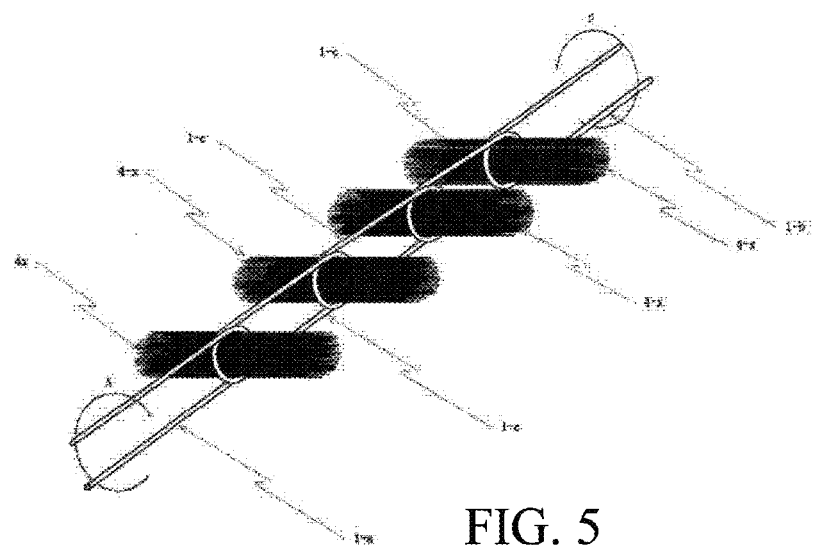
FIG. 5 is a perspective view showing a ring wire alternatively disposed between two ends of the U-shaped wires, and a fiber bundle being gripped by continuous cross-arranged loops.
Figure 6:
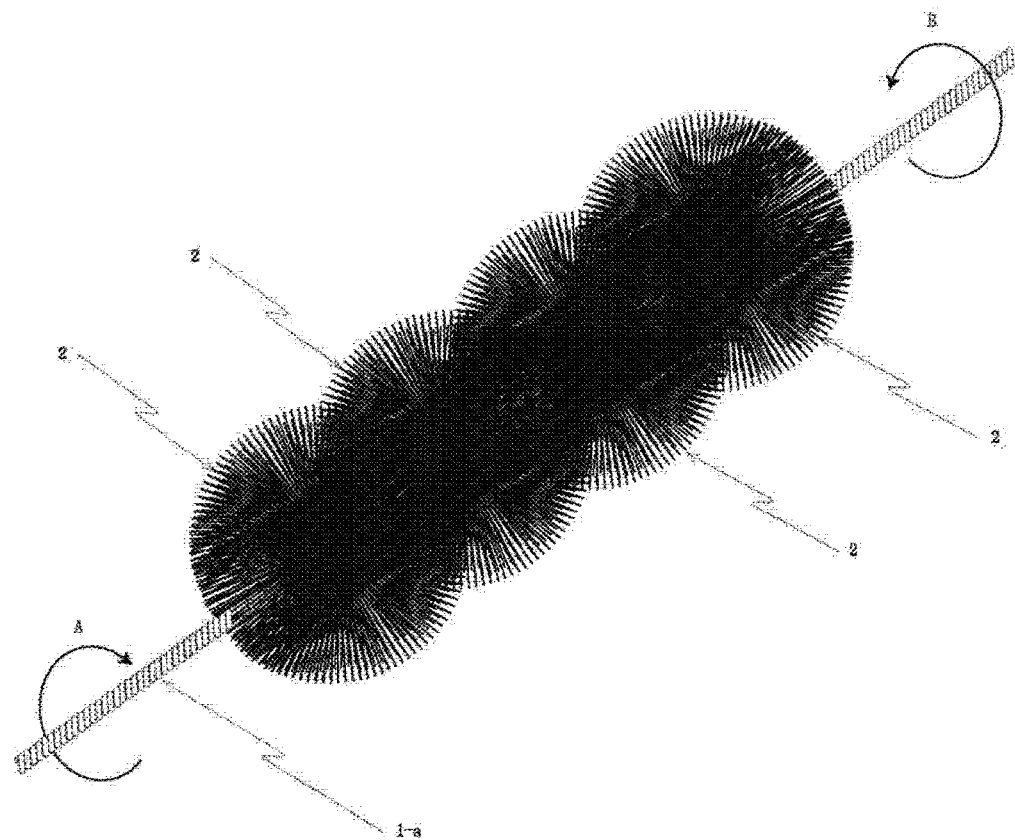
FIG. 6 is a perspective view showing a string of spherical brushes formed by pulling and twisting U-shaped wires at ends thereof to radially diverge the fiber bundle gripped by the looped wires.

For the spherical brush 2, as shown in FIG. 5, the fiber bundle 4-*x* is disposed in O-shaped loops formed by several loop-shaped wires 1-*c* crossing the U-shaped wires 1-*a*, 1-*b*, and the ends of the U-shaped wire are pulled and twisted in opposite directions A and B to obtain a string of spherical brushes, as shown in FIG. 6. The density of the longitudinal brush bristle can be controlled by adjusting the fiber length in each spherical brush. The string of spherical brushes having an identical shape are obtained by disposing the stopper 14 to compress the fiber bundle 14 according to the number of spherical brushes when the stopper 14 and U-shaped wire 1-*a* are used. The fiber bundle is compressed and diverged sequentially, and the U-shaped wires are twisted and fixed simultaneously. When the process is applied to the spherical brushes using a stopper, as shown by Y in FIG. 16, the U-shaped wires 1-*a* is loop-shaped and the fiber bundle 4 is set to pass through the stoppers n-1 to n-7. The stopper n-1, n-2, n-3 is pushed to move in directions m-1, m-2, m-3 sequentially so that the fiber bundle 4 radially diverges. When the U-shaped wires 1-*a* and the stopper n-3 are held, the stopper n-4 screws two wires 1-*a* in the direction A, whereby the stopper n-3 is fixed and the stopper n-4 is pulled in direction m-3 to determine the distance between the stoppers n-3 and n-4. Similarly, when the stopper n-5 is pushed in direction m-5, the stopper n-5 is held and the stopper n-6 is twisted in the direction A, whereby the stopper n-5 resists the repulsion caused by the compressed fiber bundle 4. For the stopper n-6 fixed by the U-shaped wires 1-*a*, the stopper n-7 is pushed, and the U-shaped wires 1-*a* is twisted to fix the stopper n-7 to maintain the cylindrical shape and obtain a teeth gap brush having brush bristles at a front portion.

The distance between the spherical brushes is determined by the positions of the stoppers. As shown in the figure, by adjusting the distances between the stoppers n-3 and n-4 and the distance between the stoppers n-5 and n-6, the spherical brush is diverged in any position as shown by Z in FIG. 15 and the brush density can also be freely adjusted to obtain a shape of a teeth gap brush having brush bristles at tips thereof.

In general, when the twisted brush has higher brush bristle density, as the bristles may fall of due to sliding between fibers, the brush bristle density is limited. The fiber bundle of the invention is compressed by wires, respectively, so that no brush bristles fall off compared with the twisted brush and provides a brush of cylinder shape having the same density as the twisted brush which has high density.

Embodiment 3

Figure 7:
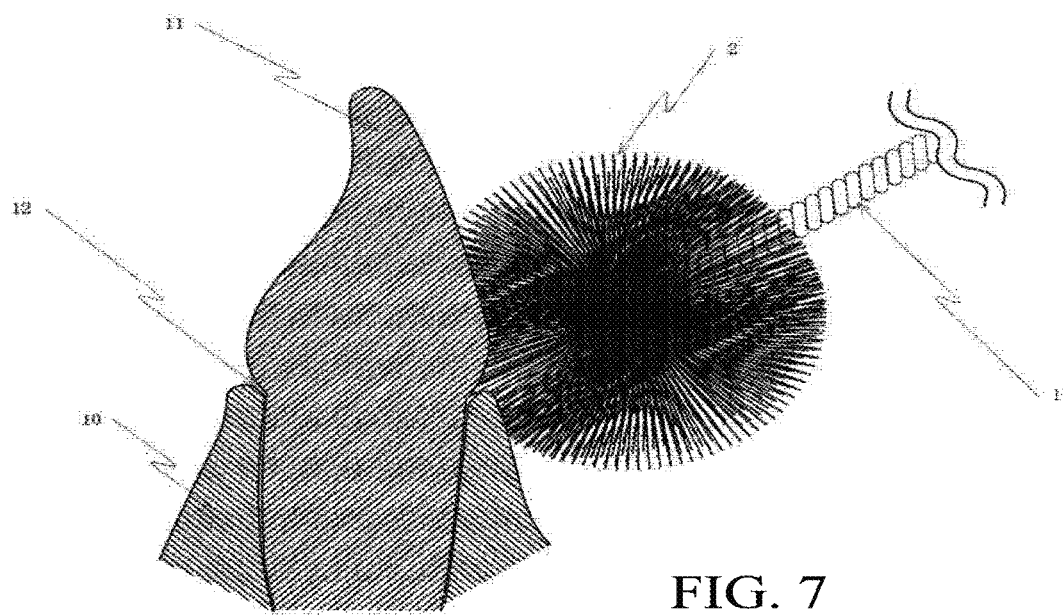
FIG. 7 is a cross section view depicting the surface of teeth and periodontal pockets cleaned by the spherical brush of the invention.
Figure 8:
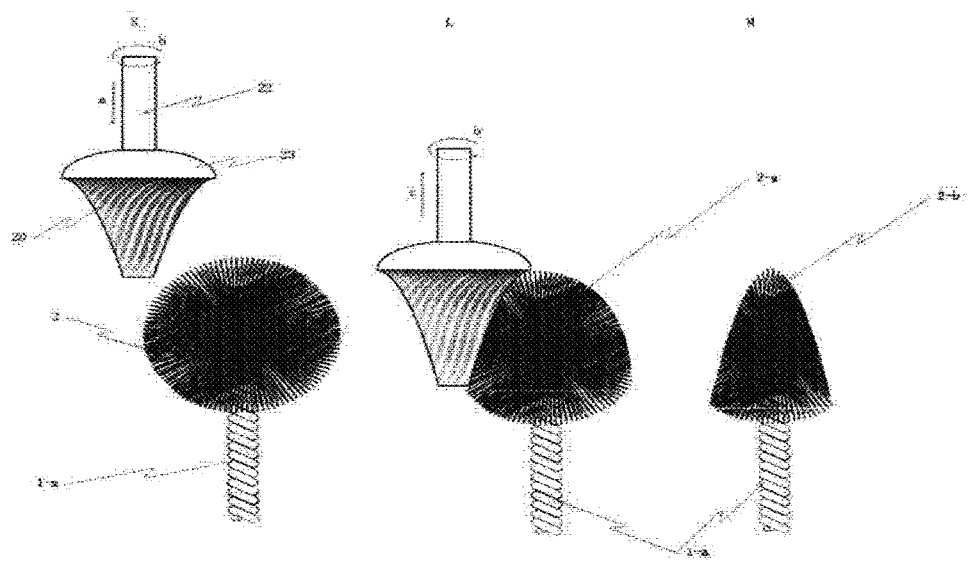
FIG. 8 depicts the spherical brush trimmed to a bullet shape.
Figure 9:
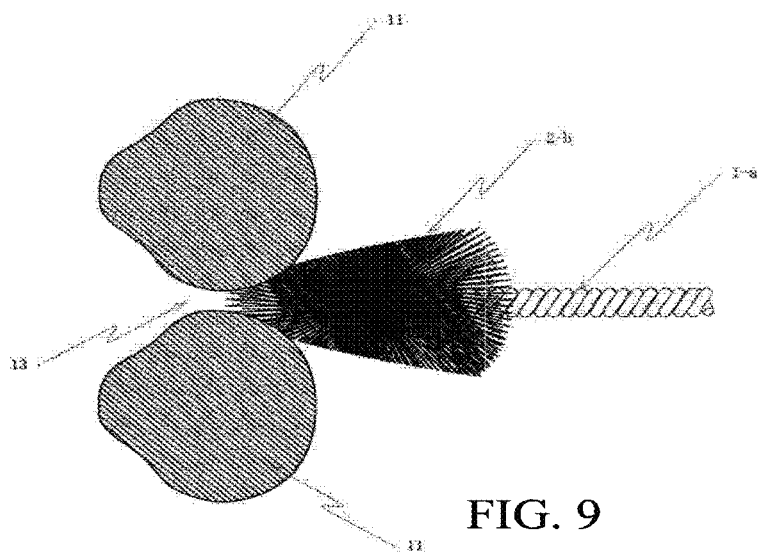
FIG. 9 depicts the bullet-shaped spherical brush inserted into teeth to clean the drum gap of teeth.
Figure 10:
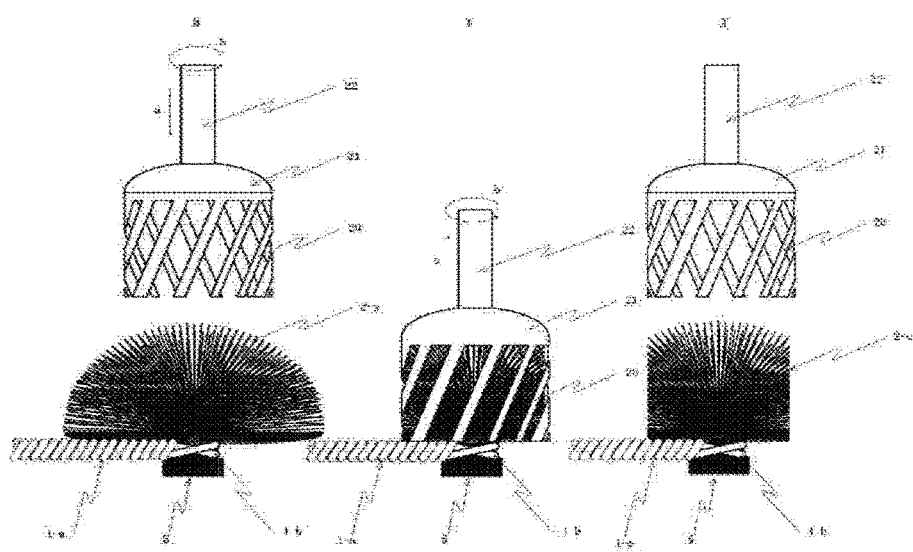
FIG. 10 depicts a trimming process for trimming a spherical brush of the invention to a cylinder shape by a trim cutter.

When the spherical brush is applied to cleaning oral cavity, as shown in FIG. 7, the brush bristle enters the gum slots in any inserting direction to perform complete cleaning. Furthermore, as shown in FIG. 8, the brush bristle of the spherical brush is trimmed to a bullet shape by a curved trim cutter 22. As shown in FIG. 9, a brush suitable for a drum teeth gap is provided. As radially diverged brush bristles of the bullet-shaped brush 2-*b* is the same as that of the spherical brush, it can clean the portions between teeth and the surfaces and the corner of the teeth gaps are cleaned. When the spherical brush is formed, the ends of the fiber bundle is held, the short side is melted and pressed to prevent fiber bundles from falling off to form the semispherical brush having brush bristles in one of the U-shaped wires 1-*a*, 2-*b* by pulling and twisting. A brush of a cylinder shape is formed by trimming the brush with a cylinder shaped cutter 21.

Figure 11:
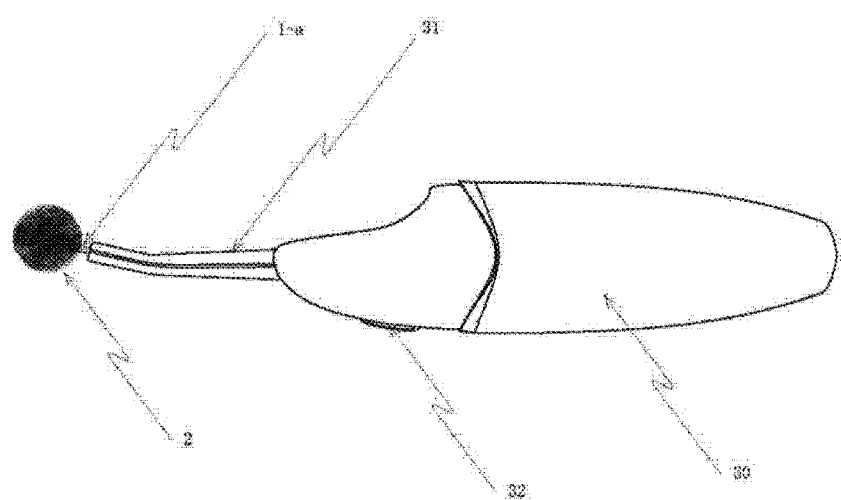
FIG. 11 is a side view of a spherical brush of one embodiment of the invention disposed on an electronic device.
Figure 12:
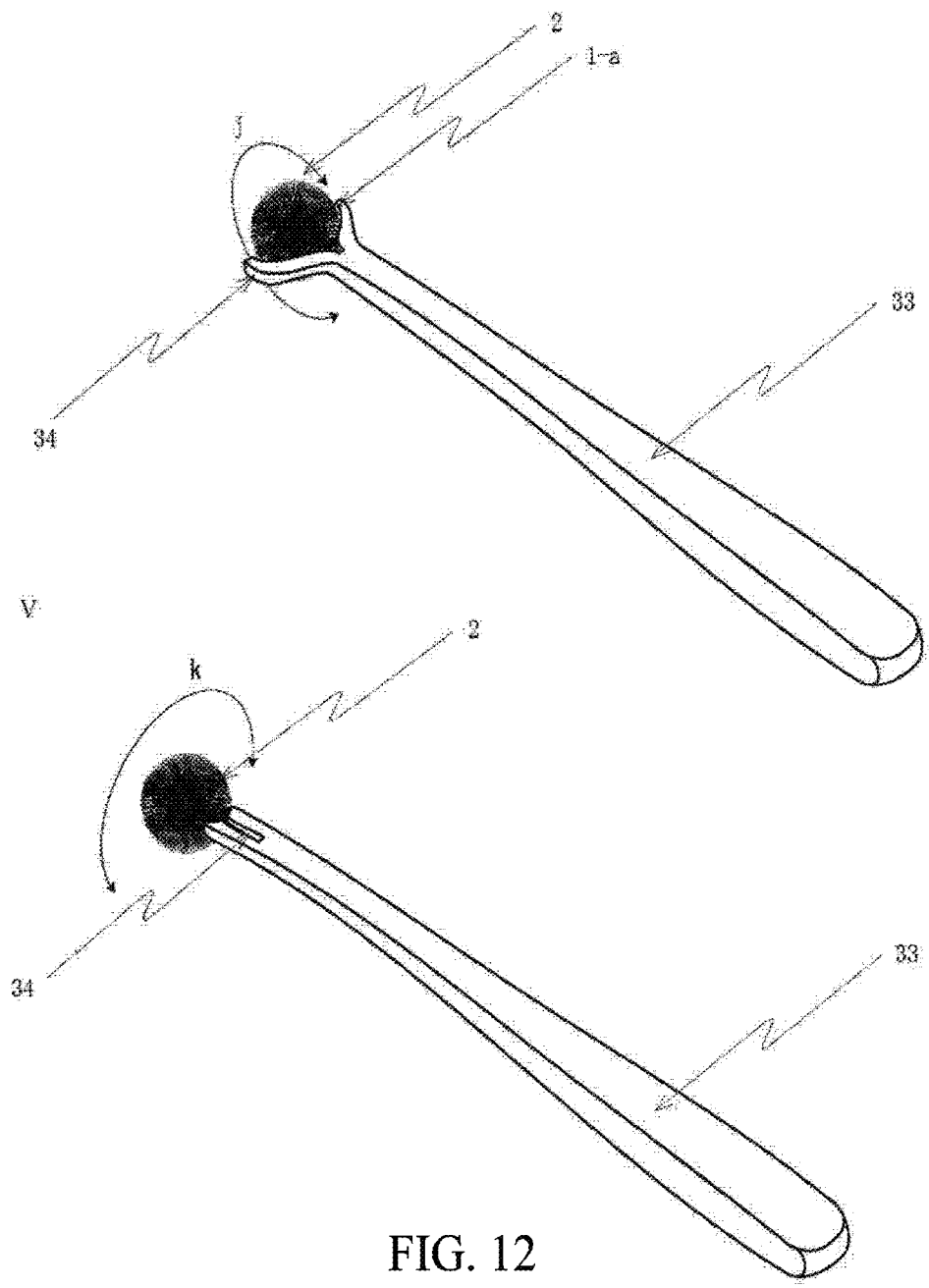
FIG. 12 is a side view showing a spherical brush of one embodiment of the invention disposed on a handle.

As shown in FIG. 11, the spherical brush is disposed on a supersonic electronic tooth brush. As the tip performing supersonic vibrations is totally covered by a brush bristle, the uncomfortable feeling caused by the vibration of the shaft heating opposing teeth like a conventional electronic tooth brush is prevented. When the spherical brush is used by hand, as shown by W in FIG. 12, the spherical brush is rotatably disposed on the U-shaped wires 1-*a*, 2-*b* in the traverse direction and rotatable in the longitudinal direction j. As shown by V in FIG. 12, a spherical brush is provided to rotate in a traverse direction k by rotatably being disposed on the U-shaped wires 1-*a*.

Embodiment 4

Figure 13:
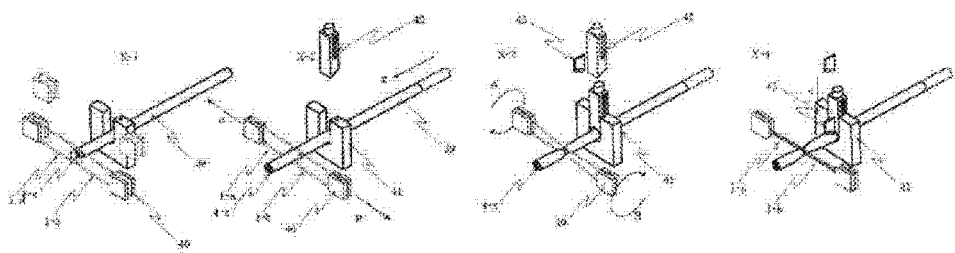
FIG. 13 is a drawing showing the manufacturing method for the invention.

During the manufacturing method for the spherical brush of various applications, when the short fibers are provided by an automatic machine, the tied long fibers are cut to short fibers and form a fiber bundle according to requirement when a clamper is inserted. However, the fibers used in the invention are very tiny and it is a problem to operate the fibers during the manufacturing process. To solve the problem, as shown in FIG. 13, a shrink film 39 with heat shrink property is disposed on the outer side of the fiber bundle 1 formed by the long fibers to obtain a fiber bundle of a predetermined diameter. The rod-shaped fiber bundle 4-*x* with the shrink film 39 is sent to the crossed portion of the U-shaped wires 1-*a*, 1-*b*, as shown by X-1, X-2, which are pulled in directions O and P by a chuck 40 and twisted in directions X-3, A and B to compress the fiber bundle 4-*x*(X-4). At this time, the fiber bundle is diverged by removing the shrink film (X-5, 6) with a shrink film cutter 43 to manufacture the spherical brush effectively as shown by X-7, 8. The shrink film 39 does not need to enclose the entire fiber bundle, and the shrink film 39 can be reciprocally disposed according to the diameter of the spherical brush. The U-shaped wires are pulled to tie the fibers and the U-shaped wires are cut to release and diverge the fibers.

As long as the U-shaped wires of the invention has enough strength and can withstand stress when the brush bristle is pulled and compressed, the material of the U-shaped wires of the invention is not limited to metal. The trimming style of the spherical brush and the shape of the melted portion are not limited to the embodiments illustrated above. They can be modified. Similarly, when the spherical brush of the invention is disposed on various devices, the shape can be varied according to various applications.

COMMERCIAL UTILIZATION

Although the examples of the spherical brush of the invention in the described embodiments is a stationary or rotatable brush used as a tooth brush or an electronic brush, the rotatable brush of the invention is not limited to being a tooth brush. The rotatable brush can also applied to a teeth gap brush, face brush, cloth cleaning brush, bed cleaning brush, jewel grinding brush, buff grinding brush, fan brush of a static cleaner for a copier, cleaning brush, or make-up brush. In particularly, when the spherical brush is applied to a static cleaner, the fan can be made of a resin which comprises tiny carbon particles and has good electronic conductivity.

What is claimed is:
1. A method for manufacturing a tooth brush, comprising:
defining a compression portion substantially at a center of a fiber bundle comprising a plurality of short fibers in a longitudinal direction by crisscrossing a first and a second U-shaped wires to form an O-looped shape portion in which the plurality of short fibers is arranged; and
pulling the first and the second wires in opposite directions while twisting in opposite directions so as to reduce a cross-section of the O-looped shape portion and compress the plurality of short fibers such that the plurality of short fibers is diverged radially from the compression portion to form a substantially spherical brush, wherein each of the first and the second wires is respectively twisted upon itself.

2. A method for manufacturing a tooth brush of claim 1, further comprising the step of trimming the plurality of short fibers of the substantially spherical brush into a bullet shape.

3. A method for manufacturing a tooth brush, comprising:
defining a compression portion substantially at a center of a fiber bundle comprising a plurality of short fibers in a longitudinal direction by mounting a stopper fixing a folded U-shaped wire at a predetermined portion of the wire to form a loop-shaped portion in which the plurality of short fibers are arranged;
pulling while twisting two ends of the wire while the stopper is held so as to reduce a cross-section of the loop shaped portion and compress the plurality of short fibers by the wire and the stopper such that the plurality of short fibers is diverged radially from the compression portion to form a substantially spherical brush, wherein the wire is twisted upon itself; and
trimming the plurality of short fibers of the substantially spherical brush into a bullet shape.

4. A tooth brush comprising:
a plurality of short fibers; and
a first wire and a second wire together defining a compression portion substantially at a center of the plurality of the short fibers in a longitudinal direction, wherein the compression portion is formed by providing the first and the second wires in a U-shaped form, and crisscrossing the first and the second wires to form an O-looped shape portion in which the plurality of short fibers is arranged, wherein the first and the second wires are pulled and twisted in opposite directions to reduce a cross-section of the O-looped shape portion and compress the plurality of short fibers such that the plurality of short fibers is diverged radially from the compression portion to form a substantially spherical brush, and wherein each of the first and the second wires is respectively twisted upon itself.

5. The tooth brush as claimed in claim 4, wherein the first wire is cut after the twisting and pulling, and the second wire extends in one direction from the compression portion in a twisted state.

6. The tooth brush as claimed in claim 4, wherein the first and the second wires extend in opposite directions from the compression portion in a twisted state.

7. A tooth brush comprising:
a plurality of short fibers; and
a first wire and a second wire together defining a compression portion which is a predetermined portion of the plurality of short fibers, wherein the compression portion is formed by providing the first and the second wires in a U-shaped form, and crisscrossing the first and the second wires to form an O-looped shape portion in which the plurality of short fibers is arranged, wherein the first and the second wires are pulled and twisted in opposite directions to reduce a cross-section of the O-looped shape portion and compress the plurality of short fibers such that the plurality of short fibers is diverged radially from the compression portion, wherein each of the first and the second wires is respectively twisted upon itself, and wherein the plurality of short fibers is trimmed to form a substantially bullet shaped brush.

8. The tooth brush as claimed in claim 7, wherein the first wire is cut after the twisting and pulling, and the second wire extends from the compression portion through a portion of the bullet shaped brush having a widest cross-section in a twisted state.

9. A tooth brush comprising:
a plurality of short fibers; and
a first wire, a second wire and at least one additional wire defining a plurality of compression portions at a plurality of fixed portions in a longitudinal direction of the wire, wherein the compression portions are formed by providing the first and the second wires in a U-shaped form and the at least one additional wire in a loop-shaped form, crisscrossing the first, second and the at least one additional wires with the first and the second wires in U-shaped form at ends thereof to form a plurality of O-looped shape portions in which the plurality of short fibers are arranged, wherein the first and the second wires in U-shaped form are pulled and twisted in opposite directions to reduce respective cross-sections of the O-looped shape portions and compress the plurality of short fibers such that they are diverged radially from the respective compression portions to form a substantially spherical brush at each fixed portion;

wherein each of the first and the second wires is respectively twisted upon itself; and wherein the spherical brush formed at each fixed portion overlaps and connects with adjacent ones.

* * * * *